United States Patent
Mullins et al.

(10) Patent No.: US 9,585,581 B1
(45) Date of Patent: Mar. 7, 2017

(54) REAL-TIME BIOMETRIC DETECTION OF OSCILLATORY PHENOMENA AND VOLTAGE EVENTS

(71) Applicant: DAQRI, LLC, Los Angeles, CA (US)

(72) Inventors: Brian Mullins, Sierra Madre, CA (US); Teresa Ann Nick, Woodland Hills, CA (US); Laura Berman, Venice, CA (US); Arye Barnehama, Venice, CA (US); Eric Douglas Lundquist, Los Angeles, CA (US)

(73) Assignee: DAQRI, LLC, Los Angeles, CA (US)

( * ) Notice: Subject to any disclaimer, the term of this patent is extended or adjusted under 35 U.S.C. 154(b) by 0 days.

(21) Appl. No.: 14/870,900

(22) Filed: Sep. 30, 2015

(51) Int. Cl.
*A61B 5/04* (2006.01)
*A61B 5/0478* (2006.01)
*A61B 5/00* (2006.01)

(52) U.S. Cl.
CPC ........ *A61B 5/04012* (2013.01); *A61B 5/0478* (2013.01); *A61B 5/6803* (2013.01); *A61B 5/7257* (2013.01)

(58) Field of Classification Search
None
See application file for complete search history.

(56) References Cited

U.S. PATENT DOCUMENTS

| | | | |
|---|---|---|---|
| 2005/0197590 A1* | 9/2005 | Osorio | A61B 5/048 600/544 |
| 2006/0111644 A1* | 5/2006 | Guttag | A61B 5/048 600/544 |
| 2006/0200034 A1* | 9/2006 | Ricci | H03H 17/0201 600/513 |
| 2014/0249424 A1* | 9/2014 | Fan | A61B 5/0255 600/473 |

* cited by examiner

*Primary Examiner* — Etsub Berhanu
(74) *Attorney, Agent, or Firm* — Schwegman Lundberg & Woessner, P.A.

(57) ABSTRACT

A system and method for identifying changes in a state or activity is described. A real-time event monitoring application, implemented in a hardware processor, computes features over varying sampling periods, which are stored in cascading buffers. The various sampling periods enable determination of trends of a computed feature, comparison of the trends of the computed feature with trends of other features, normalization of the computed feature based on the same or different features at the same or different time scales, scaling of the normalized computed feature relative to other features at the same or different time scale, and identification of a change in state or activity based on a scaled normalized computed feature.

14 Claims, 13 Drawing Sheets

REAL-TIME BIOMETRIC DETECTION OF OSCILLATORY PHENOMENA AND VOLTAGE EVENTS

TECHNICAL FIELD

The subject matter disclosed herein generally relates to the processing of data. Specifically, the present disclosure addresses systems and methods for analyzing data in real-time using embedded or mobile systems with relatively low memory and/or computational power.

BACKGROUND

The subject matter disclosed herein generally relates to the processing of data. Specifically, the present disclosure addresses systems and methods for analyzing data in real-time using embedded or mobile systems with relatively low memory and/or computational power.

A fundamental problem with real-time biometric feedback of oscillatory phenomena, such as electroencephalography (EEG) and electrocardiography (ECG), is the long duration analytics timeframe for data that are most informative in the frequency domain (e.g., 1 second for one cycle in the case of low delta) versus the requirement for much faster feedback times for user utility (<=250 ms). In addition, detection of biologically-relevant voltage deflection events requires comparison of incoming data to an ongoing, often shifting, baseline.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
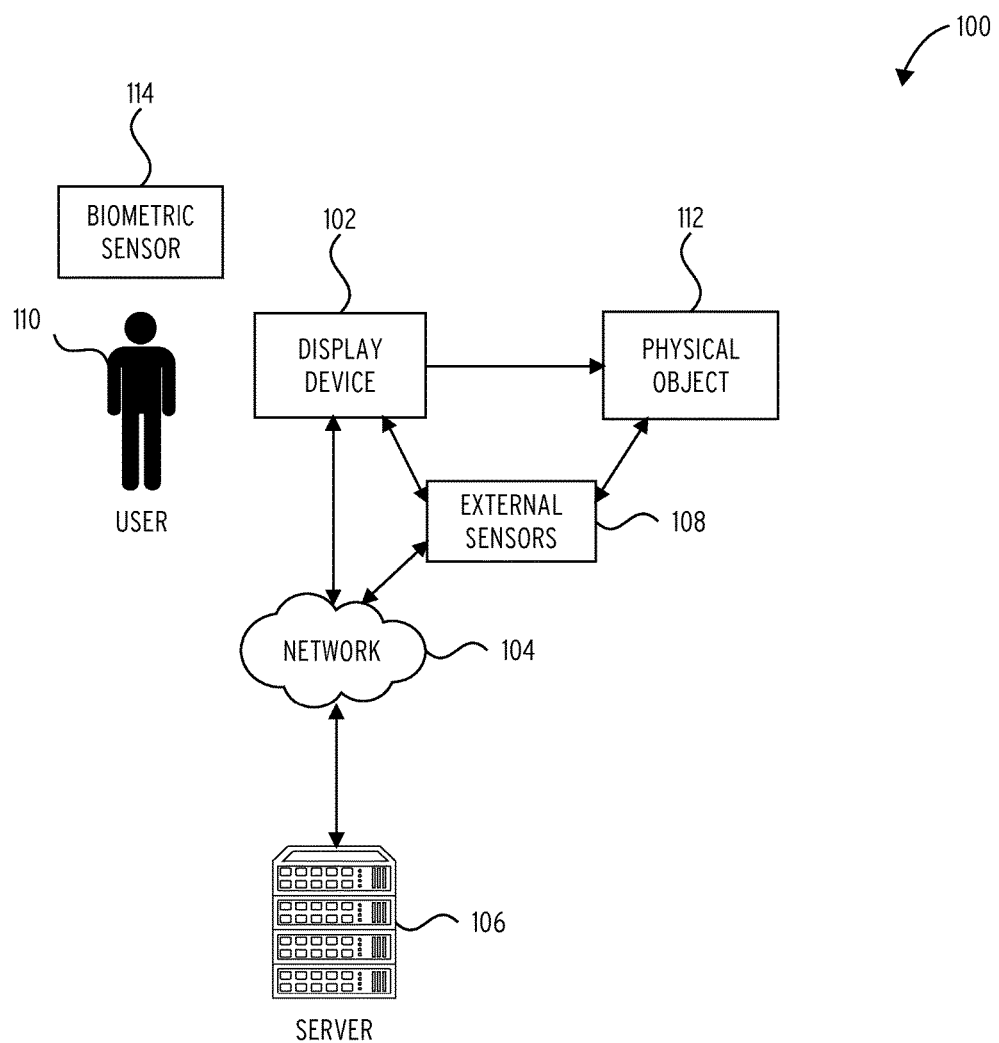
FIG. 1 is a block diagram illustrating an example of a network environment suitable for real-time biometric detection, according to some example embodiments.

Example methods and systems are directed to identifying state shifts and events in real-time, generating and changing virtual content based on the state shifts and events. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

A method and system for less CPU- and memory-intensive analytics for real-time biometric feedback of oscillatory phenomena, such as electroencephalography (EEG) and electrocardiography (ECG), is described. The system describes a staged or cascading buffering system, where measures of central tendency or variability across shorter timescales are saved to higher-order, longer-duration buffers. For example, delta power can be computed by summing the spectral amplitude from 1-4 Hz from an FFT on 1 second of data. These values can be computed every 100-msec (using the last 1 second of data) and saved to a first order buffer that contains, say, 5 values, or measures for the most previous 500-msec. Every analytics cycle, the central tendency of this small, most recent buffer can be computed and saved as a single value to a longer-term buffer. To robustly detect changes in delta from baseline, the central tendency of the recent buffer can be compared to the longer-term buffer. For very long time-scales, this general design can be extrapolated to N-order filters.

The design can be optimized in time by altering the FFT window, the FFT sampling period, and the number and size of buffers. For detection of various states or events, different frequencies or frequency ratios can be saved to the cascading buffers. The use of cascading buffers saves on memory and CPU-intensive analytics in a resource poor system, such as a mobile device. In particular, the use of cascading buffers can be implemented in a computing display device, such as an augmented reality display device including an augmented reality application.

Augmented reality applications allow a user to experience information, such as in the form of a three-dimensional virtual object displayed in a transparent lens or in a non-transparent display. In the case of a non-transparent display, the virtual object is displayed as an overlay on a picture of a physical object captured by a camera of a device. The physical object may include a visual reference that the augmented reality application can identify. The three-dimensional virtual object may be selected based on the recognized visual reference or a state of the user. A rendering of the visualization of the three-dimensional virtual object may be based on a position of the display relative to the visual reference. The virtual object may change based on a state of a user. For example, if a real-time algorithm identifies that the user is fixing his/her gaze, the display device may display a first virtual object. If the real-time algorithm identifies that the user is looking around, the display device may display a second virtual object different from the first virtual object.

Figure 6:
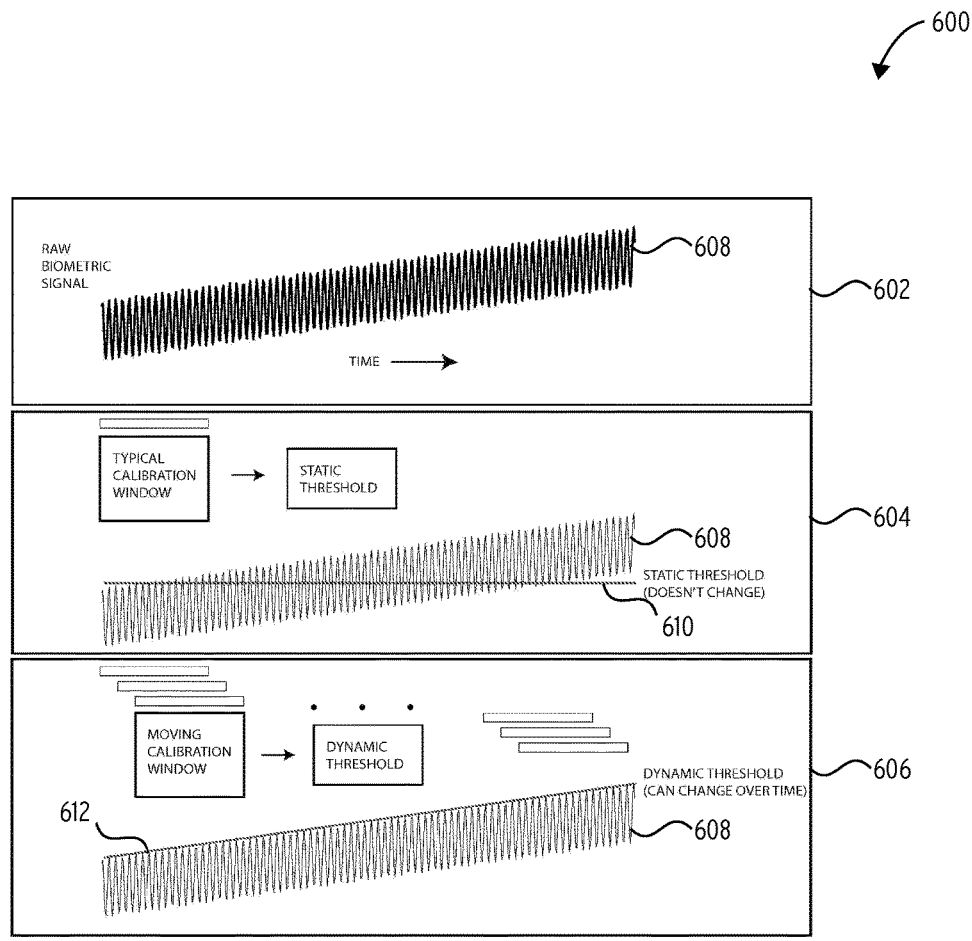
FIG. 6 illustrates examples of baselines in accordance with one embodiment.

Behaviors and neural rhythms of a user may be determined by recording voltage and performing a computation on the recorded data without requiring training data to calibrate the algorithm. The present application describes an algorithm that is a real-time scale invariant method for transforming electroencephalography (EEG) and other biometric data taken from electrodes on the user into a single normalized value that identifies events and state shifts by detecting deviations in time and frequency domains from an accumulated baseline. The algorithm works by tracking time series data in the time and frequency domains over several timescales simultaneously. Cascading buffers of metrics at several time scales enable comparison of long-timescale baselines with shorter-timescale values without the costs in memory and processing power that are required for storage of continuous data across long timescales. Cascading buffers also dynamically adjust to shifts in baselines, which is not the case for more typical scenarios in which a fixed calibration period at the beginning of a biometric recording are compared to all data that follow. For example, in FIG. 6, a simple sine wave with low frequency drift is analyzed using a threshold computed using traditional means and cascading buffers. Using a typical calibration window at the beginning of the trace yields a static threshold that does not change. The subsequent drift results in events that would typically be "noise" being classed as "above threshold". In contrast, with cascading buffers, a moving calibration window is enabled, which resets the threshold dynamically and allows the threshold to track the low frequency drift, reducing the possibility for false positives above threshold.

The present algorithm differs greatly from standard approaches in that calibration is not required and baseline drifts are dynamically adjusted. The algorithm measures the relative change of metrics over small periods of time relative to longer periods of time (stored in different buffers) and analyzes the directional shifts to calculate whether or not the metric is increasing or decreasing at some arbitrary point in time. The relationship between the long-term and current trends (e.g., the central tendencies of a short-term buffer divided by a longer-term buffer) is used to detect short-term changes in voltage that indicate behavioral events and changes in state and activity levels. Events include, for example, eye and facial movements and muscle contractions. States include stressed, relaxed, focused, and not focused. Activities include eating, meditating, and sleeping.

A system and method for identifying a change in neural and/or behavioral state in real-time and generating a virtual object based on the event is described. In an example embodiment, a display device includes at least two electrodes, a camera, and a hardware processor comprising a real-time cascaded buffer application and an augmented reality application. The two electrodes record voltage deflections that reflect behaviors and brain wave activity. The real-time cascaded buffer application computes a ratio of a first and a second type of wave over a sampling period, determines a trend of the computed ratio by taking the central tendency of a sampling buffer, compares the trend of the computed ratio with a longer-term trend of the same or a different wave or ratio stored in a second buffer, normalizes the computed ratio based on the longer-term time-scale, and identifies a neural or behavioral event or state change based on this normalization. For example, the focus training application identifies one of two visual focus or gaze fixation states. The two visual focus states include a fixed and non-fixed gaze.

In another example embodiment, the real-time cascaded buffer application computes a first mean power of the first type of wave over a sampling period n from sample values stored in buffer 1 and stores the mean in buffer 2 (e.g., size 5), a second mean power of the first type of wave over a second longer sampling period (e.g., 5n) based on stored values in buffer 2 and stores the mean in buffer 3 (e.g., size 10), a third mean power of the first type of wave over a third, even longer sampling period (e.g., 50n) based on values from previous calculations stored in buffer 3.

In another example embodiment, the device includes a camera configured to capture a reference identifier from a physical object. The augmented reality application identifies a virtual object associated with the reference identifier, displays the virtual object in a display of the device, in response to a relative movement between the device and the physical object caused by a user, and modifies the virtual object based on the real-time state or activity of a user of the device. The real-time application identifies a change in the state or activity of a user of the device. The augmented reality application modifies the virtual object based on the change in the state or activity of the user of the device.

In another example embodiment, the augmented reality application communicates the reference identifier via a network to a remote server. The remote server includes virtual object data associated with the reference identifier. The augmented reality application receives the virtual object data at the device, and displays the virtual image in the display using the virtual object data. In response to a relative movement between the device and the physical object caused by a user, the augmented reality application modifies the virtual image. The brain activity application receives brain or behavioral activity data of the user and changes a state of the virtual object in the virtual landscape based on the brain or behavioral activity data.

In another example embodiment, a non-transitory machine-readable storage device may store a set of instructions that, when executed by at least one processor, causes the at least one processor to perform the method operations discussed within the present disclosure.

Certain example embodiments are described herein as including modules. Modules may constitute software modules (e.g., code stored or otherwise embodied in a machine-readable medium or in a transmission medium), hardware modules, or any suitable combination thereof. A "hardware module" is a tangible (e.g., non-transitory) physical component (e.g., a set of one or more processors) capable of performing certain operations and may be configured or arranged in a certain physical manner. In various example embodiments, one or more computer systems or one or more hardware modules thereof may be configured by software (e.g., an application or portion thereof) as a hardware module that operates to perform operations described herein for that module.

In some example embodiments, a hardware module may be implemented mechanically, electronically, hydraulically, or any suitable combination thereof. For example, a hardware module may include dedicated circuitry or logic that is permanently configured to perform certain operations. A hardware module may be or include a special-purpose processor, such as a field programmable gate array (FPGA) or an ASIC. A hardware module may also include programmable logic or circuitry that is temporarily configured by software to perform certain operations. As an example, a hardware module may include software encompassed within a CPU or other programmable processor. It will be appreciated that the decision to implement a hardware module mechanically, hydraulically, in dedicated and permanently configured circuitry, or in temporarily configured circuitry (e.g., configured by software) may be driven by cost and time considerations.

Accordingly, the phrase "hardware module" should be understood to encompass a tangible entity that may be physically constructed, permanently configured (e.g., hardwired), or temporarily configured (e.g., programmed) to operate in a certain manner or to perform certain operations described herein. Furthermore, as used herein, the phrase "hardware-implemented module" refers to a hardware module. Considering example embodiments in which hardware modules are temporarily configured (e.g., programmed), each of the hardware modules need not be configured or instantiated at any one instance in time. For example, where a hardware module includes a CPU configured by software to become a special-purpose processor, the CPU may be configured as respectively different special-purpose processors (e.g., each included in a different hardware module) at different times. Software (e.g., a software module) may accordingly configure one or more processors, for example, to become or otherwise constitute a particular hardware module at one instance of time and to become or otherwise constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over suitable circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory (e.g., a memory device) to which it is communicatively coupled. A further hardware module may then, at a later time, access the memory to retrieve and process the stored output. Hardware modules may also initiate communications with input or output devices, and can operate on a resource (e.g., a collection of information from a computing resource).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module in which the hardware includes one or more processors. Accordingly, the operations described herein may be at least partially processor-implemented, hardware-implemented, or both, since a processor is an example of hardware, and at least some operations within any one or more of the methods discussed herein may be performed by one or more processor-implemented modules, hardware-implemented modules, or any suitable combination thereof.

Moreover, such one or more processors may perform operations in a "cloud computing" environment or as a service (e.g., within a "software as a service" (SaaS) implementation). For example, at least some operations within any one or more of the methods discussed herein may be performed by a group of computers (e.g., as examples of machines that include processors), with these operations being accessible via a network (e.g., the Internet) and via one or more appropriate interfaces (e.g., an application program interface (API)). The performance of certain operations may be distributed among the one or more processors, whether residing only within a single machine or deployed across a number of machines. In some example embodiments, the one or more processors or hardware modules (e.g., processor-implemented modules) may be located in a single geographic location (e.g., within a home environment, an office environment, or a server farm). In other example embodiments, the one or more processors or hardware modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and their functionality presented as separate components and functions in example configurations may be implemented as a combined structure or component with combined functions. Similarly, structures and functionality presented as a single component may be implemented as separate components and functions. These and other variations, modifications, additions, and improvements fall within the scope of the subject matter herein.

Some portions of the subject matter discussed herein may be presented in terms of algorithms or symbolic representations of operations on data stored as bits or binary digital signals within a memory (e.g., a computer memory or other machine memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "accessing," "processing," "detecting," "computing," "calculating," "determining," "generating," "presenting," "displaying," or the like refer to actions or processes performable by a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The following embodiments describe various example embodiments of methods, machine-readable media, and systems (e.g., machines, devices, or other apparatus) discussed herein.

FIG. 1 is a block diagram illustrating an example of a network environment suitable for real-time biometric detection, according to some example embodiments.

A network environment 100 includes a display device 102 and a server 106, communicatively coupled to each other via a network 104. The display device 102 and the server 106 may each be implemented in a computer system, in whole or in part, as described below with respect to FIG. 13.

The server 106 may be part of a network-based system. For example, the network-based system may be or include a cloud-based server system that provides additional information, such as 3D models or other virtual objects, to the display device 102.

A user 110 may wear the display device 102 and look at a physical object 112 in a real world physical environment. The user 110 may be a human user (e.g., a human being), a machine user (e.g., a computer configured by a software program to interact with the display device 102), or any suitable combination thereof (e.g., a human assisted by a machine or a machine supervised by a human). The user 110 is not part of the network environment 100, but is associated with the display device 102. For example, the display device 102 may be a computing device with a camera and a transparent display such as a tablet, smartphone, or a wearable computing device (e.g., helmet or glasses). In another example embodiment, the computing device may be hand held or may be removably mounted to the head of the user 110. In one example, the display may be a screen that displays what is captured with a camera of the display device 102. In another example, the display of the display device 102 may be transparent or semi-transparent such as in lenses of wearable computing glasses or the visor or a face shield of a helmet.

The user 110 may be a user of an AR application in the display device 102 and at the server 106. The AR application may provide the user 102 with an AR experience triggered by identified objects (e.g., physical object 112) in the physical environment. For example, the physical object 112 include identifiable objects such as a 2D physical object (e.g., a picture), a 3D physical object (e.g., a factory machine), a location (e.g., at the bottom floor of a factory), or any references (e.g., perceived corners of walls or furniture) in the real world physical environment. The AR application may include computer vision recognition to determine corners, objects, lines, letters, and so forth.

A biometric sensor 114 may be removably coupled to the user 110. The biometric sensor 114 may be external to the display device 102 or part of the display device 102. For example, the display device 102 may be a helmet with a visor with the biometric sensor 114 (e.g., electrodes) disposed inside the helmet. The AR application in the display device 102 may generate or change virtual content based on a real-time analysis of data from the biometric sensor 114.

In one example embodiment, the objects in the image are tracked and recognized locally in the display device 102 using a local context recognition dataset or any other previously stored dataset of the AR application of the display device 102. The local context recognition dataset module may include a library of virtual objects associated with real-world physical objects or references. In one example, the display device 102 identifies feature points in an image of the physical object 112. The display device 102 may also identify tracking data related to the physical object 112 (e.g., GPS location of the display device 102, orientation, distance to the physical object 112). If the captured image is not recognized locally at the display device 102, the display device 102 can download additional information (e.g., 3D model or other augmented data) corresponding to the captured image, from a database of the server 106 over the network 104.

In another example embodiment, the physical object 112 in the image is tracked and recognized remotely at the server 106 using a remote context recognition dataset or any other previously stored dataset of an AR application in the server 106. The remote context recognition dataset module may include a library of virtual objects or augmented information associated with real-world physical objects or references.

External sensors 108 may be associated with, coupled to, related to the physical object 112 to measure a location, status, and characteristics of the physical object 112. Examples of measured readings may include and but are not limited to weight, pressure, temperature, velocity, direction, position, intrinsic and extrinsic properties, acceleration, and dimensions. For example, external sensors 108 may be disposed throughout a factory floor to measure movement, pressure, orientation, and temperature. The external sensors 108 can also be used to measure a location, status, and characteristics of the display device 102 and the user 110. The server 106 can compute readings from data generated by the external sensors 108. The server 106 can generate virtual indicators such as vectors or colors based on data from external sensors 108. Virtual indicators are then overlaid on top of a live image or a view of the physical object 112 in a line of sight of the user 110 to show data related to the object 116. For example, the virtual indicators may include arrows with shapes and colors that change based on real-time data. The visualization may be provided to the physical object 112 so that the display device 102 can render the virtual indicators in a display of the display device 102. In another example embodiment, the virtual indicators are rendered at the server 106 and streamed to the display device 102.

The external sensors 108 may include other sensors used to track the location, movement, and orientation of the display device 102 externally without having to rely on sensors internal to the display device 102. The sensors 112 may include optical sensors (e.g., depth-enabled 3D camera), wireless sensors (Bluetooth, Wi-Fi), GPS sensors, and audio sensors to determine the location of the user 110 wearing the display device 102, distance of the user 110 to the external sensors 108 (e.g., sensors placed in corners of a venue or a room), the orientation of the display device 102 to track what the user 110 is looking at (e.g., direction at which the display device 102 is pointed, e.g., display device 102 pointed towards a player on a tennis court, display device 102 pointed at a person in a room).

In another example embodiment, data from the external sensors 108 and internal sensors in the display device 102 may be used for analytics data processing at the server 106 (or another server) for analysis on usage and how the user 110 is interacting with the physical object 112 in the physical environment. Live data from other servers may also be used in the analytics data processing. For example, the analytics data may track at what locations (e.g., points or features) on the physical or virtual object the user 110 has looked, how long the user 110 has looked at each location on the physical or virtual object, how the user 110 wore the display device 102 when looking at the physical or virtual object, which features of the virtual object the user 110 interacted with (e.g., such as whether the user 110 engaged with the virtual object), and any suitable combination thereof. The display device 102 receives a visualization content dataset related to the analytics data. The display device 102 then generates a virtual object with additional or visualization features, or a new experience, based on the visualization content dataset.

Any of the machines, databases, or devices shown in FIG. 1 may be implemented in a general-purpose computer modified (e.g., configured or programmed) by software to be a special-purpose computer to perform one or more of the functions described herein for that machine, database, or device. For example, a computer system able to implement any one or more of the methodologies described herein is discussed below with respect to FIG. 13. As used herein, a "database" is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 1 may be combined into a single machine, and the functions described herein for any single machine, database, or device may be subdivided among multiple machines, databases, or devices.

The network 104 may be any network that enables communication between or among machines (e.g., server 106), databases, and devices (e.g., device 101). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

Figure 2:
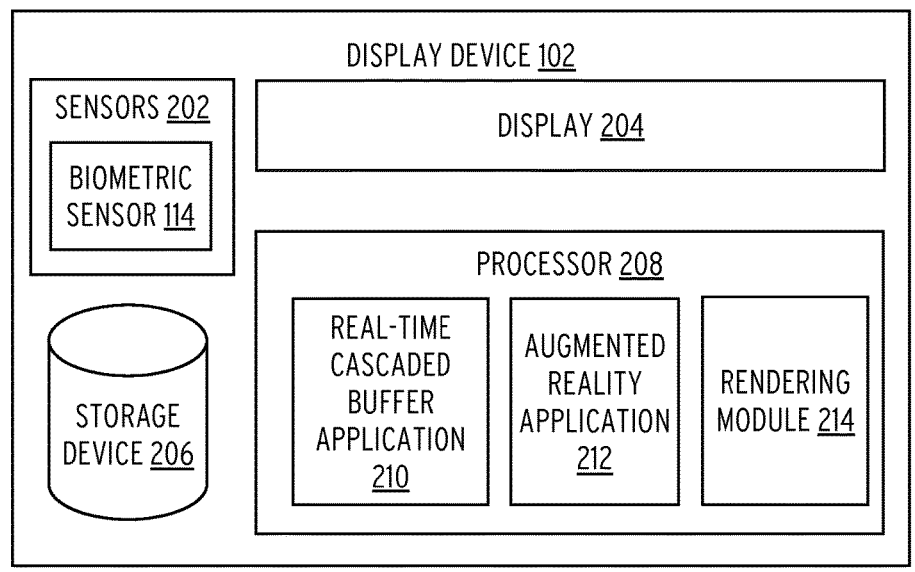
FIG. 2 is a block diagram illustrating an example embodiment of modules (e.g., components) of a display device suitable for analyzing biometric data in real-time and generating augmented reality content based on the findings.

FIG. 2 is a block diagram illustrating an example embodiment of modules (e.g., components) of a display device suitable for analyzing data in real-time and generating augmented reality content based on the findings.

The display device 102 includes sensors 202, a display 204, a processor 208, and a storage device 206. For example, the display device 102 may include a mobile computing device (e.g., a smartphone, a tablet, a laptop) or a wearable computing device (e.g., a smart helmet, a smart visor, a smart watch or any other computing device worn by the user 110).

In one example embodiment, the sensors 202 may include the biometric sensor 114 (e.g., at least two electrodes) to measure electrical activity from a human. For example, the biometric sensor 114 may include a first and a second electrode connected to a forehead of the user 110. The biometric sensor 114 may be used to measure EEG (electroencephalography) waves of the brain, EMG (electromyography) waves of muscles, ECG (electrocardiography) waves of the heart, and EOG (electro-oculogram) waves of eyes. The biometric sensor 114 can also be used to monitor brainwaves through EEG by detecting electrical signals about the user's present state or activity. The biometric sensor 114 may be implemented, for example, by using a headset or a helmet worned by the user 110. In another example, the biometric sensor 114 can be used to monitor facial muscles to detect facial expressions of the user 110.

In another example embodiment, the sensors 202 may also include: an optical sensor (e.g., a charged-coupled device (CCD)), an orientation sensor (e.g., gyroscope), an audio sensor (e.g., a microphone), a thermometer, an infrared camera, a barometer, and/or a humidity sensor. For example, the display device 102 may include a front-facing camera for tracking eyes movement and facial expression of the user, and a rear-facing camera for capturing a picture or a video of a physical object (or another displayed virtual object). It is noted that the sensors 202 described herein are for illustration purposes and the sensors 202 are thus not limited to the one described. In another example, sensors 202 may not be physically connected to the display device 102 but are instead coupled to the display device 102 via wireless means such as Wi-Fi and Bluetooth® or through human body networks.

The display 204 includes, for example, a touchscreen display configured to receive a user input via a contact on the touchscreen display. In another example, the display 204 includes a screen or monitor configured to display images generated by the processor 208. In another embodiment, the display 204 may be a transparent, a translucent, or a see-through display.

The processor 208 includes a real-time cascaded buffer application 210, an augmented reality application 212, a rendering module 214. The real-time cascaded buffer application 210 determines a state or activity (e.g., stressed, relaxed) of the user 110 in real-time based on outputs from the biometric sensor 114. The state or activity may be based on the intensity or pattern of the outputs of the biometric sensor 114. The state or activity may be classified in a spectrum where the state or activity may be predefined relative to the range of outputs from the biometric sensor 114. For example, an output between a range of 0 to 0.3 may be categorized as relaxed. An output between a range of 0.7 to 1 may be categorized as stressed.

In one example embodiment, the real-time cascaded buffer application 210 identifies the intensity or pattern of the different types of electric waves discharged by the brain of the user 110 over a short period of time (a sampling period). At least two electrodes may be placed on the forehead of the user 110. Algorithms may be configured to measure different types of waves. For example, Delta waves are most present during sleep. Theta waves are associated with deep relaxation and internal focus. Frontal alpha waves reflect active suppression of sensory inputs. Beta and Gamma waves occur when actively thinking or problem-solving. The real-time cascaded buffer application 210 identifies a state or activity of the user based on the outputs of the biometric sensor 114. For example, the real-time cascaded buffer application 210 may use the biometric sensor 114 (e.g., EEG electrodes) alone or in combination with other sensors from sensors 202 (e.g., microphone, camera, and heart rate monitor). The real-time cascaded buffer application 210 is described in more detail in FIG. 3 and FIG. 4.

The augmented reality application 212 generates a display of a virtual object (three-dimensional or two-dimensional model) in the display 204. In another example, the augmented reality application 212 generates a display of the virtual object overlaid on an image of the physical object 112 captured by the sensors 202. The virtual object may be selected or generated based on the state or activity of the user as determined by the real-time cascaded buffer application 210. The virtual object and features of the virtual object may be further manipulated based on a change in the state or activity of the user.

In another example embodiment, the augmented reality application 212 receives data from sensors 202 (e.g., receive an image of the physical object 112) and identifies and recognizes the physical object 112 using machine-vision recognition techniques. The augmented reality application 212 then retrieves from the storage device 206 AR content associated with the physical object 112. In one example embodiment, the augmented reality application 212 identifies a visual reference (e.g., a logo or QR code) on the physical object 112 (e.g., a chair) and tracks the location of the visual reference within the display 204 of the display device 102. The visual reference may also be referred to as a marker and may consist of an identifiable image, symbol, letter, number, machine-readable code. For example, the visual reference may include a bar code, a quick response (QR) code, or an image that has been previously associated with the virtual object.

The rendering module 214 renders virtual objects based on data from sensors 202. For example, the rendering module 214 renders a display of a virtual object (e.g., a door with a color based on the temperature inside the room as detected by sensors from HMDs inside the room) based on a three-dimensional model of the virtual object (e.g., 3D model of a virtual door) associated with the physical object 112 (e.g., a physical door). In another example, the rendering module 214 generates a display of the virtual object overlaid on an image of the physical object 112 captured by a camera of the display device 102. The virtual object may be further manipulated (e.g., by the user 110) by moving the physical object 112 relative to the display device 102. Conversely, the display of the physical object 112 may be manipulated (e.g., by the user 110) by moving the display device 102 relative to the physical object 112.

In one example embodiment, the rendering module 214 identifies the physical object 112 (e.g., a physical telephone) based on data from sensors 202 and external sensors 108, accesses virtual functions (e.g., increase or lower the volume of a nearby television) associated with physical manipulations (e.g., lifting a physical telephone handset) of the physical object 112, and generates a virtual function corresponding to a physical manipulation of the physical object 112.

In another example embodiment, the rendering module 214 determines whether the captured image matches an image locally stored in the storage device 206 that includes a local database of images and corresponding additional information (e.g., three-dimensional model and interactive features). The rendering module 214 retrieves a primary content dataset from the server 106, generates and updates a contextual content dataset based on an image captured with the display device 102.

The storage device 206 stores data from the biometric sensor 114 and sensors 202, a database of long-term biometric baselines for that user, if available, and for a set of similar users, a database of visual references, virtual objects corresponding to the visual references, features of the virtual objects corresponding to the virtual objects, and corresponding states or activities. The features of the virtual objects can change with the state or activity of the user. For example, the color of the virtual chair can change from blue to red as the user becomes more stressed. The virtual chair may be displayed in a blue color if the user is relaxed.

The storage device 206 further includes a database of visual references (e.g., images, visual identifiers, features of images) and corresponding experiences (e.g., three-dimensional virtual objects, interactive features of the three-dimensional virtual objects). For example, the visual reference may include a machine-readable code or a previously identified image (e.g., a picture of a screwdriver). The previously identified image of the screwdriver may correspond to a three-dimensional virtual model of the screwdriver that can be viewed from different angles by manipulating the position of the display device 102 relative to the picture of the screwdriver. Features of the three-dimensional virtual screwdriver may include selectable icons on the three-dimensional virtual model of the screwdriver. An icon may be selected or activated using a user interface on the display device 102.

In another example embodiment, the storage device 206 includes a primary content dataset, a contextual content dataset, and a visualization content dataset. The primary content dataset includes, for example, a first set of images and corresponding experiences (e.g., interaction with three-dimensional virtual object models). For example, an image may be associated with one or more virtual object models. The primary content dataset may include a core set of images of the most popular images determined by the server 106. The core set of images may include a limited number of images identified by the server 106. For example, the core set of images may include the images depicting covers of the ten most popular machines and their corresponding experiences (e.g., virtual objects that represent the ten most popular physical objects viewed by the display device 102). In another example, the server 106 may generate the first set of images based on the most popular or often scanned images received at the server 106. Thus, the primary content dataset does not depend on objects or images scanned by the rendering module 214 of the display device 102.

The contextual content dataset includes, for example, a second set of images and corresponding experiences (e.g., three-dimensional virtual object models) retrieved from the server 106. For example, images captured with the display device 102 that are not recognized (e.g., by the server 106) in the primary content dataset are submitted to the server 106 for recognition. If the captured image is recognized by the server 106, a corresponding experience may be downloaded at the display device 102 and stored in the contextual content dataset. Thus, the contextual content dataset relies on the context in which the display device 102 has been used. As such, the contextual content dataset depends on objects or images scanned by the rendering module 214.

In one embodiment, the display device 102 may communicate over the network 102 with the server 106 to retrieve a portion of a database of visual references, corresponding three-dimensional virtual objects, and corresponding interactive features of the three-dimensional virtual objects. The network 102 may be any network that enables communication between or among machines, databases, and devices (e.g., the display device 102). Accordingly, the network 102 may be a wired network, a wireless network (e.g., a mobile or cellular network), or any suitable combination thereof. The network 104 may include one or more portions that constitute a private network, a public network (e.g., the Internet), or any suitable combination thereof.

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 3:
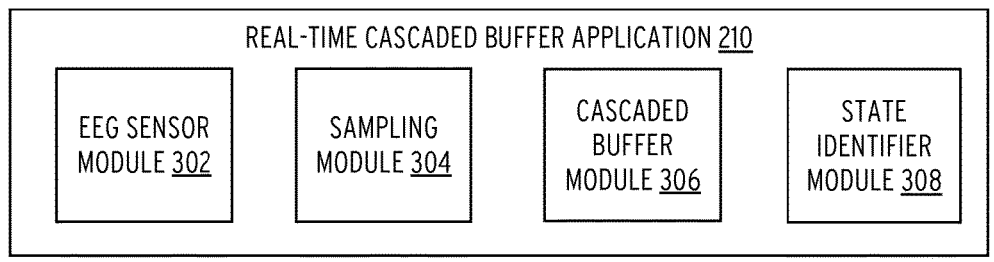
FIG. 3 is a block diagram illustrating an example embodiment of modules (e.g., components) of a real-time cascaded buffer application suitable for analyzing biometric data in real-time.

FIG. 3 is a block diagram illustrating an example embodiment of modules (e.g., components) of the real-time cascaded buffer application 210 suitable for analyzing biometric data in real-time.

The real-time cascaded buffer application 210 includes an EEG sensor module 302, a sampling module 304, and a cascaded buffer module 306.

The EEG sensor module 302 captures outputs from the biometric sensor 114. The EEG sensor module 302 may capture electric waves generated by a brain of the user 110 by using EEG electrodes in contact with the forehead of the user 110. As previously described, the EEG sensor module 302 may also capture outputs from other types of sensors (e.g., sensors 202) such as a heart rate monitor or a facial muscle monitor to further supplement outputs from the EEG electrodes. In another embodiment, the sensors 202 may include a camera to detect the gaze of the user and determine where the user is look on the display 204.

The sampling module 304 captures data from the biometric sensor 114 during a sampling period (e.g., 4 ms) into a first A buffer. The sample rate may be, for example, 250 Hz. Thus, the sampling module 304 captures a sample of outputs from the sensors at the sample rate during a sampling period. The sample outputs may then be used as a baseline or a reference for the user that can shift over time as the buffer cycles.

The cascaded buffer module 306 receives data from the sampling module 304 and also data from sensors 202 (and optionally, external sensors 108). For example, the mean of the first A buffer of size n from the sampling module 304 may be saved into a second B buffer that contains the means for the last m time sampling periods (size n), enabling the trend across m*n samples to be monitored. Because only means are saved, the buffer is smaller than a buffer that contains m*n samples, yet provides similar information. To obtain data across a still longer time scale, a third C buffer of size p may contain the last p means of the B buffer, enabling tracking of trends across m*n*p samples. This general cascaded buffer design can be extrapolated to successively larger time scale buffers, enabling tracking of time series simultaneously across several timescales at relatively low cost in terms of computation and memory. In addition, different features of time series (such as frequency content or voltage deflections classed as eyeblinks) can be tracked at different timescales, enabling selective and compact calculation of means and other statistics only on timescales that are relevant for those features. For example, the cascaded buffer module 306 may measure the spectral power of electrical signals of Alpha waves at time intervals of 10 sec in combination with the heart rate at time intervals of 20 sec of the user 110 to determine the user's relaxed state of mind. In another example embodiment, the value may be based on a statistical computation (e.g., average or median) of one or more outputs from selected sensors.

The state identifier module 308 may determine that the user 110 is relaxed or stressed. In another example embodiment, the state identifier module 308 may determine a change in state or activity of the user 110 based on changes to the data from the cascaded buffer module 306. For example, the state identifier module 308 may determine that the user 110 who was previously relaxed is now in a state of stress. For example, a 20% decrease in heart rate variability, a measure of Respiratory Sinus Arrhythmia and stress, could be interpreted as the user becoming stressed. To obtain the percent change in heart rate variability, the mean of a short-term 60-sec buffer could be divided by the mean of a longer-term 1-hour cascaded buffer and multiplied by 100.

Figure 4:
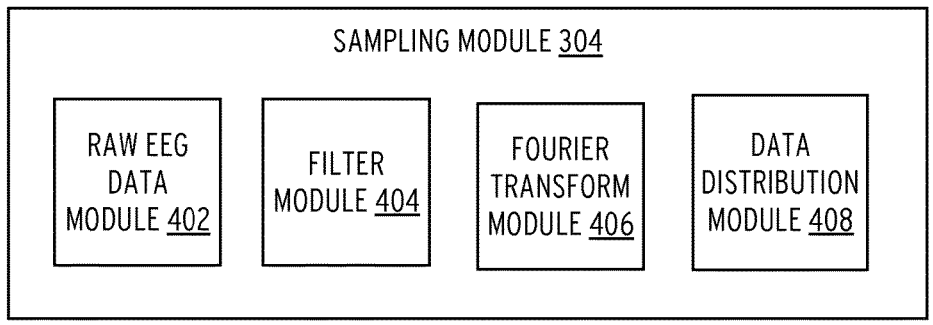
FIG. 4 is a block diagram illustrating an example embodiment of modules (e.g., components) of a sampling module.

FIG. 4 is a block diagram illustrating an example embodiment of modules (e.g., components) of a sampling module.

The sampling module 304 processes the sampled raw EEG data with a raw EEG data module 402, a filter module 404, a data distribution module 408, and a Fourier transform module 406. The raw EEG data module 402 receives the sampling sampled EEG data. The raw EEG data may include data from the different types of waves (e.g., alpha, beta, theta, delta).

The filter module 404 applies a filter to attenuate electrical interference. For example, the filter module 404 performs a 50 or 60 Hz Infinite Impulse Response (IIR) Notch Filter (Q=~0.717) (depending on location) to attenuate electrical interference and then applies an IIR Bandpass Filter with a range of either 1-35 Hz, 1-42 Hz, 1-48 Hz or 1-50 Hz. In one example implementation, 1-49 Hz is the default of range (Q=~0.717) to pass relevant frequencies in the EEG signal.

The Fourier transform module 406 performs a sliding window Fourier Transform on the filtered data. For example, the Fourier transform module 406 slides over samples using a duration of 1-second (e.g., 256 samples, padded as necessary to achieve a power of 2).

The data distribution module 408 computes, for example, a central tendency and/or variability metric over the sampling period. Depending on the distribution of the measured feature, median (for non-parametric data) or mean (for parametric data) may be computed. For example, the mean of the alpha power output from the Fourier transform over a 60-sec sampling period may be computed.

Figure 5:
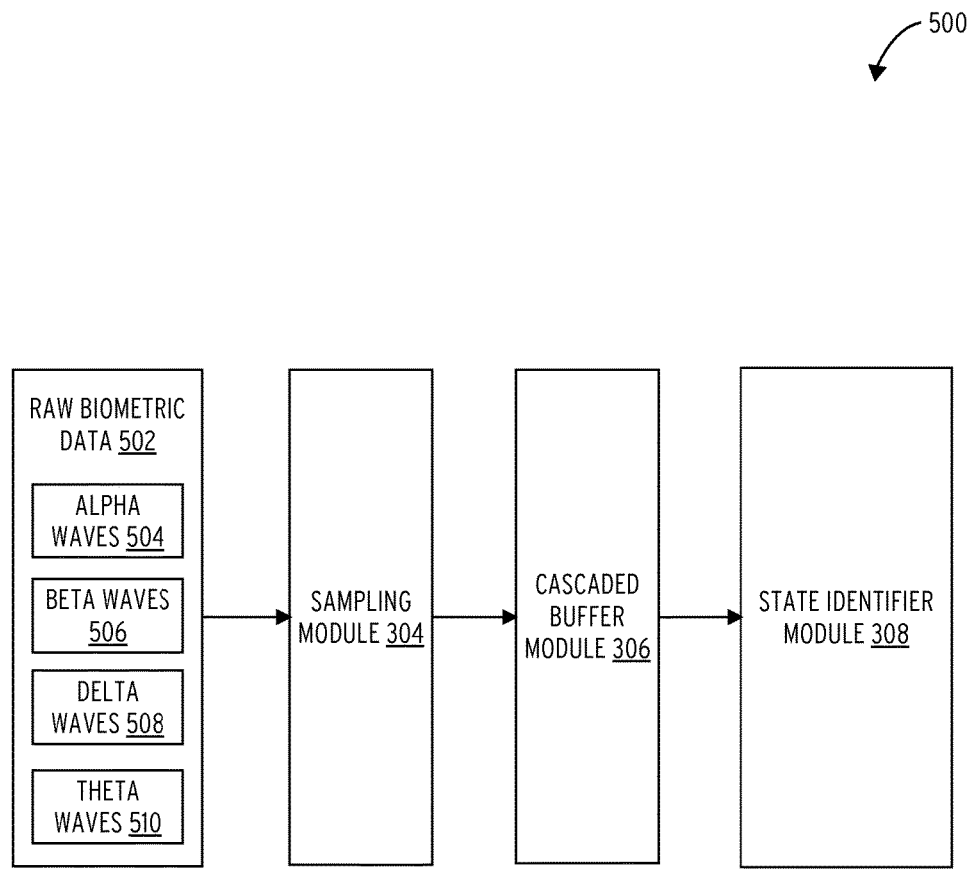
FIG. 5 is a block diagram illustrating an example operation of a real-time cascaded buffer, in accordance with one example embodiment.

FIG. 5 is a block diagram illustrating an example operation of a real-time cascaded buffer, in accordance with one example embodiment.

The raw biometric data 502 includes data from the different types of waves: alpha waves 504, beta waves 506, delta waves 508, and theta waves 510 (slow wave, gamma, high-gamma waves may also be included, depending on the application).

The sampling module 304 processes raw biometric data 502 with digital signal processing techniques. For example, EEG data would be filtered, subjected to a Fourier Transform, and then analyzed for spectral power in specific frequency bands of neural relevance.

The cascaded buffer module 306 generates a cascaded buffer from the outputs of the sampling module. Upon initialization, the shortest-term buffer A is filled with sampled data points. Once buffer A is filled, a central tendency or variability metric is computed and placed in buffer B. Buffer A may then be flushed and the process of filling A may begin again. The process can continue to longer time frames, such that when buffer B is filled, a central tendency or variability metric is computed and placed in buffer C. Each successive filter contains data over a longer time frame.

The state identifier module 308 identifies a state of the user 110 based on computed changes to multiple biometric measures from the cascaded buffer module 306. For example, a change in focal attention could be assessed by measuring the percent change in frontal lobe beta:alpha in a short-term buffer relative to a longer-term cascaded buffer. A decrease in beta:alpha would indicate a decrease in focal attention.

Example 602 illustrates a raw biometric signal in the form of a simple sine wave 608 with low frequency drift. In Example 604, a static threshold 610 is computed using traditional means. Using a typical calibration window at the beginning of the trace yields a static threshold that does not change. The subsequent drift results in events that would typically be "noise" being classed as "above threshold".

Example 606 illustrates a dynamic threshold 612 computed using cascading buffers. In contrast, with cascading buffers, a moving calibration window is enabled, which resets the threshold dynamically and allows the dynamic threshold 612 to track the low frequency drift, reducing the possibility for false positives above threshold.

Figure 7:
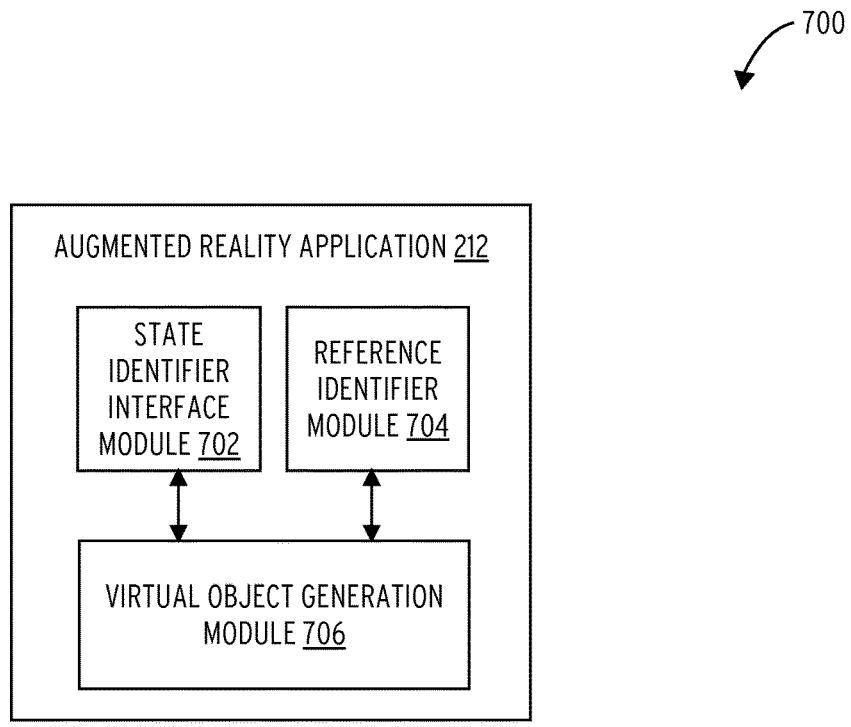
FIG. 7 is a block diagram illustrating an example embodiment of modules (e.g., components) of an augmented reality application.

FIG. 7 is a block diagram illustrating an example embodiment of modules (e.g., components) of an augmented reality application. The augmented reality application 212 includes a state identifier interface module 702, a reference identifier module 704, and a virtual object generation module 706.

The state identifier interface module 702 identifies a computed state or activity of the user 110 based on the state identifier module 308 of the real-time cascaded buffer application 210. For example, the real-time cascaded buffer application 210 may indicate that the user is relaxed. The real-time cascaded buffer application 210 may also identify that a change in the level of relaxation of the user.

The reference identifier module 704 identifies a visual reference on the physical object 112 captured by sensors 202 (and optionally external sensors 108). For example, a camera of the display device 102 captures an image of the physical object 112, such as a page on a newspaper. The page on the newspaper may include an article and a picture. The picture may have been already identified as a visual reference in the storage device 206. The picture may be associated with a corresponding three-dimensional model of an object (e.g., a virtual sofa).

The virtual object generation module 706 generates and displays a visualization of a three-dimensional virtual object engaged with an image of the physical object captured by the sensors 202 of the display device 102 (e.g., the virtual sofa floats and rotates on top of the magazine page). The virtual object may be based on the visual reference (e.g., a furniture ad in the magazine page). In one embodiment, each virtual object may be uniquely associated with a visual reference. The virtual object generation module 706 renders the visualization of the virtual object based a position of the display device 102 relative to the visual reference. In another example embodiment, attributes of the virtual object may be based on the state or activity of the user 110. For example, the virtual object generation module 706 may generate a 3D model of a virtual blue color sofa when the state identifier interface module 702 indicates that the user is relaxed. Similarly, the virtual object generation module 706 may generate a 3D model of a red color sofa when the state identifier interface module 702 indicates that the user 110 is stressed.

In yet another example embodiment, the virtual object generation module 706 generates a virtual object based on a change in the level of relaxation of the user 110. For example, a blue color car may morph into a red color sofa when the state of mind of the user 110 indicates that the user 110 is getting stressed.

Figure 8:
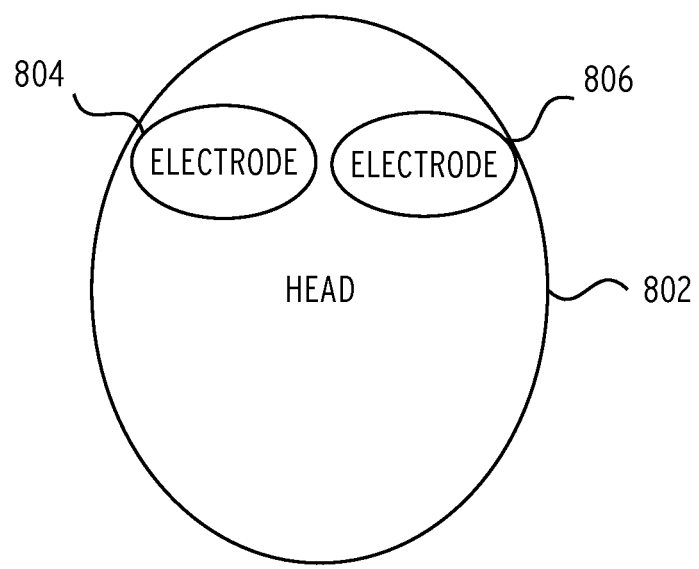
FIG. 8 is a diagram illustrating a top view of a head of a user with electrodes applied to the head of the user.

FIG. 8 is a diagram illustrating a top view of a head of a user with electrodes applied to the head 802 of the user 110 (other reference electrodes may be placed around the head and body). Computations may be applied to data from both electrodes relative to their references individually or both simultaneously. The latter returns two event streams. The computation algorithms may use data from both electrodes and may also dynamically switch between the electrode 804 and electrode 806 depending of the quality of the data from the respective electrodes.

Figure 9:
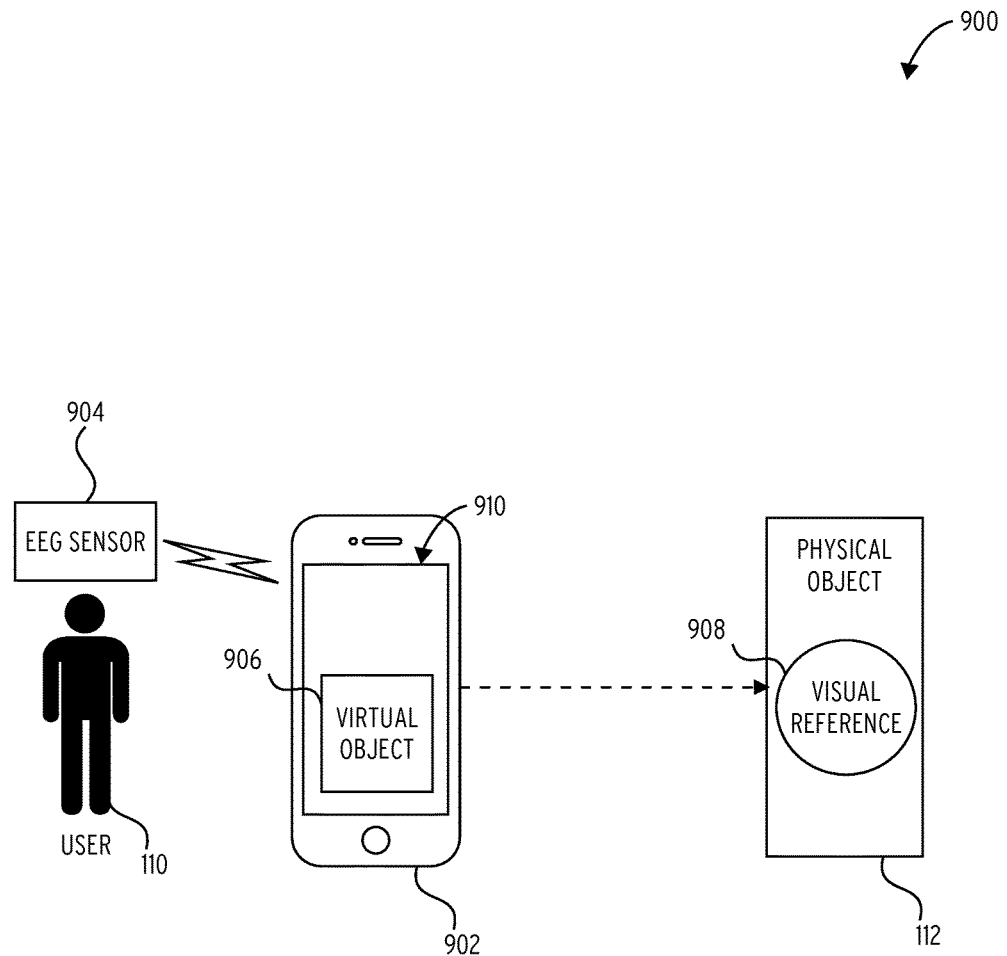
FIG. 9 is a diagram illustrating an example operation of a display device suitable for generating augmented reality content based a real-time analysis of biometric data, according to some example embodiments.

FIG. 9 is a diagram illustrating an example operation of a display device suitable for generating augmented reality content based a real-time analysis of biometric data, according to some example embodiments.

The user 110 is equipped with an EEG sensor 904 (e.g., electrode 804, 706 connected to the forehead of the user 110. As previously described, EEG sensor 904 include other types of measuring devices for measuring skin temperature and heart rate activity among others. Electrodes 704, 706 may be physically coupled via wires to a mobile device 902 (e.g., smart phone). In another example, electrodes 704, and 706 may communicate with the mobile device 902 wirelessly using wireless communication means (e.g., WiFi, Bluetooth®, ZigBee®).

The user 110 points a rear camera (not shown) of the mobile device 902 towards the physical object 112 having a visual reference 908 (e.g., uniquely identifiable visual pattern or features). As previously described, the visual reference 908 may include a picture, a machine-readable code, or any other identifier unique to the augmented reality application 212 in the mobile device 902. The physical object 112 may be, for example, a page of a magazine or newspaper. In another embodiment, the physical object 112 and the visual reference 908 may be combined together (e.g., a poster or a cup). In such case, the three-dimensional physical object may be used as a visual reference. For example, a three-dimensional object such as a cup having a specific pattern or design may be used as a visual reference. The mobile device 902 captures an image or a picture of the physical object 112 and the visual reference 908 using the rear camera.

The mobile device 902 displays a virtual object 906 in a display 910 of the mobile device 902 based on the visual reference 908 and outputs from EEG sensor 904. For example, the mobile device 902 determines that the user 110 is geographically located at a particular office. The mobile device 902 determines from the EEG sensor 904 that the level of stress of the user 110 corresponds to a stressed state (as opposed to a relaxed state). In another embodiment, a front facing camera (not shown) of the mobile device 902 may further enhance and provide additional data on the state of mind of the user 110. For example, the mobile device 902 may obtain a live picture of the user 110 using the front facing camera to determine a smile or a frown. In another example, the front facing camera may be used for facial recognition to determine the identity of the user 110. The mobile device 902 may retrieve preferences from the user 110 such as, for example, favorite colors or items from a user profile (stored in the mobile device 902, or in a server of a social network service provider). In another example, the mobile device 902 determines, identifies, and manipulates the virtual object 906 to be displayed in the display based on a combination of the geographic location of the mobile device 902 (e.g., office, home, restaurant, city, country), time of capture (e.g., morning, afternoon, evening, holiday, weekend) of the visual reference 908, orientation (e.g., portrait or landscape, how close) of the mobile device 902 relative to the visual reference 908, identification of the user 110 (e.g., using facial recognition, or login information), preferences of the user 110 (e.g., favorite color, favorite type of music) social network information (e.g., number of friends, interests, proximity of friends, postings) related to the user 110, outputs from sensors 904 (e.g., EEG brain waves, EMG muscles waves, EOG eye movements, heart rate, blood pressure), and the visual reference 908.

The mobile device 902 may then display the virtual object 906 as an overlay on top of a picture of the physical object 112 based on the real-time state or activity the user 110. For example, the virtual object 906 may be a three-dimensional model of a building rendered on top of an image of the physical object 112 in the display 910 if the user 110's state of mind is identified as in a stressed state. In another example, if the user's state of mind determined to be relaxed, the mobile device 902 may generate a three-dimensional model of a vacation home rendered on top of the image of the physical object 112 in the display 910 of the mobile device 902. Thus, the mobile device 902 identifies which virtual object to display in response to the visual reference 908 and the present state or activity of the user 110.

Figure 10:
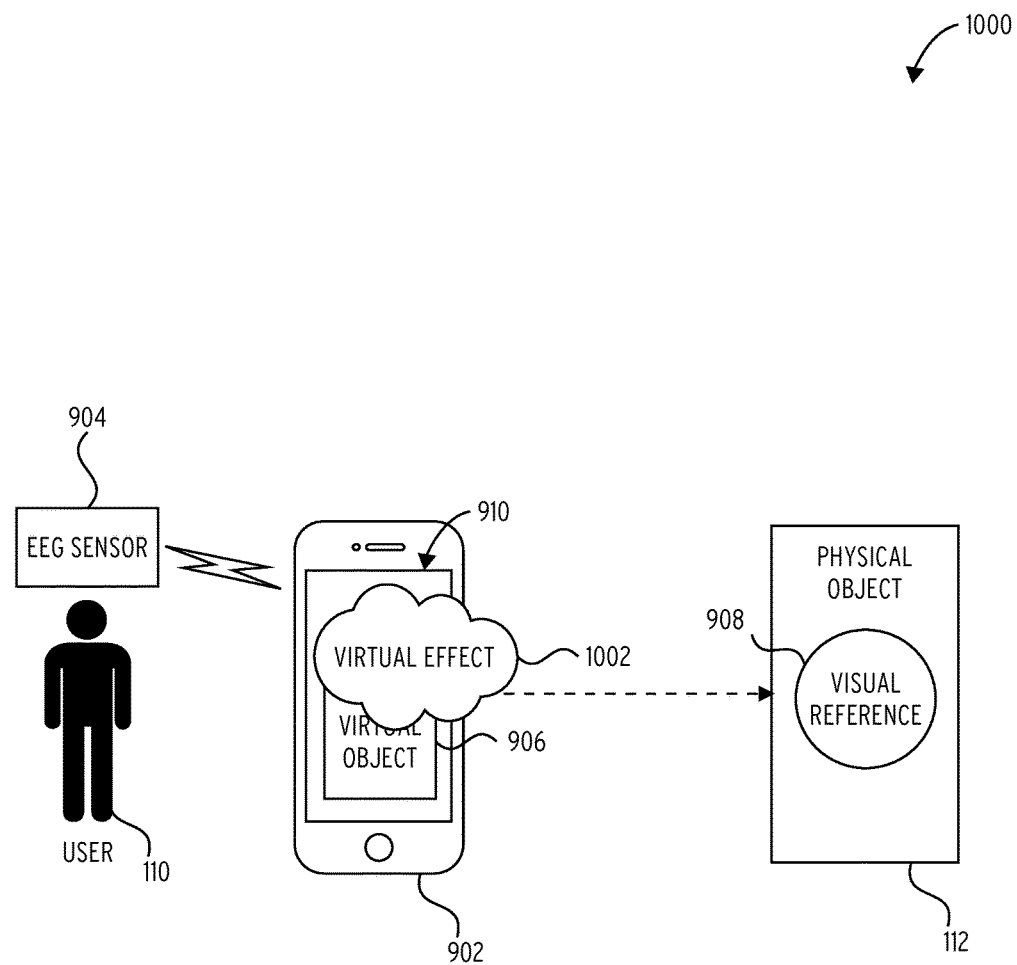
FIG. 10 is a diagram illustrating an example operation of a display device suitable for generating augmented reality content based a real-time analysis of biometric data, according to some example embodiments.

FIG. 10 is a diagram illustrating an example operation of a display device suitable for generating augmented reality content based a real-time analysis of biometric data, according to some example embodiments.

The mobile device 902 determines a change in the state of mind of the user 110 (e.g., from focused to distracted, or from relaxed to stressed). The mobile device 902 then generates a change to the virtual object 906 in the display 910 of the mobile device 902 based on the change in the state or activity of the user 110 in response to changes in outputs from EEG sensor 904 and the front facing camera of the mobile device 902. For example, virtual effect 1002 (e.g., dynamic animation of rain) may be displayed over the virtual object 906 in the display 910 when the mobile device 902 detects that the user 110 has frowned or is stressed.

As such, changes of the already displayed virtual object 906 in the display 910 are determined based on the changes in the state of mind of the user 110. In another example, the color of the virtual object 906 may change to a lighter hue when the user 110 becomes more relaxed while looking at the virtual object 906. In another example, the texture of the virtual object 906 may change to a rougher texture when the state of mind of the user 110 indicates that the user 110 is agitated.

In another example embodiment, the mobile device may include a transparent display (not shown). The transparent display may be mounted to a head of the user (e.g., via eyeglass mount or headgear mount). In another example, the transparent display may be a handheld device that the user 110 holds and looks through to see the physical object 112 located behind the transparent display. The rear facing camera of the mobile device 902 may recognize physical objects being looked by the user (e.g., by comparing an image of the physical object 112 with a reference image). In particular, the position and orientation of the transparent display with respect to the user 110 and the physical object 112 may be used to determine a line of sight of the user 110. Using the determined line of the sight of the user 110, the mobile device 902 can identify in real time which physical objects are being looked and in particular which part of the physical object the user 110 is looking.

Once the mobile device 902 identifies that the recognized physical object 112 or the part of the recognized physical object 112 corresponds to a preidentified physical object or preidentified part of the physical object 112, the mobile device 902 may trigger a corresponding action (e.g., sending an email, generating a sound, etc.) based on the state of mind of the user 110. For example, the mobile device 902 detects the user 110 is looking through the transparent display towards a bottom portion of a television set. The mobile device 902 recognizes the television set and determines that the bottom portion of the television set (being looked at by the user 110) is associated with an action corresponding to generating a communication to the television set to switch the TV on or off. If the user 110 has looked at the bottom portion of the television set for at least several seconds and the state of mind indicates that the user is relaxed, the mobile device 902 generates a corresponding signal to turn on or off the television set.

In another example, the mobile device 902 may display a virtual menu of TV channels overlaid on the physical TV set based on the state of mind of the user 110. For example, if the user 110 is excited, the virtual menu of TV channels may include sports channels and action movies. If the state of mind of the user 110 corresponds to a relaxed state, the virtual menu of TV channels may include news or music videos channels.

In another example, the user 110 may look through a transparent display of the mobile device 902 to a radio device. Similarly, a virtual menu of music channels may be displayed as a layer over the radio device based on the state of mind of the user 110. For example, the mobile device 902 displays a virtual menu showing classical or relaxing music channels when the EEG sensor 904 indicates that the user 110 is stressed. The state of mind of the user 110 may be predicted in real-time using the real-time cascaded buffer application 210.

Figure 11:
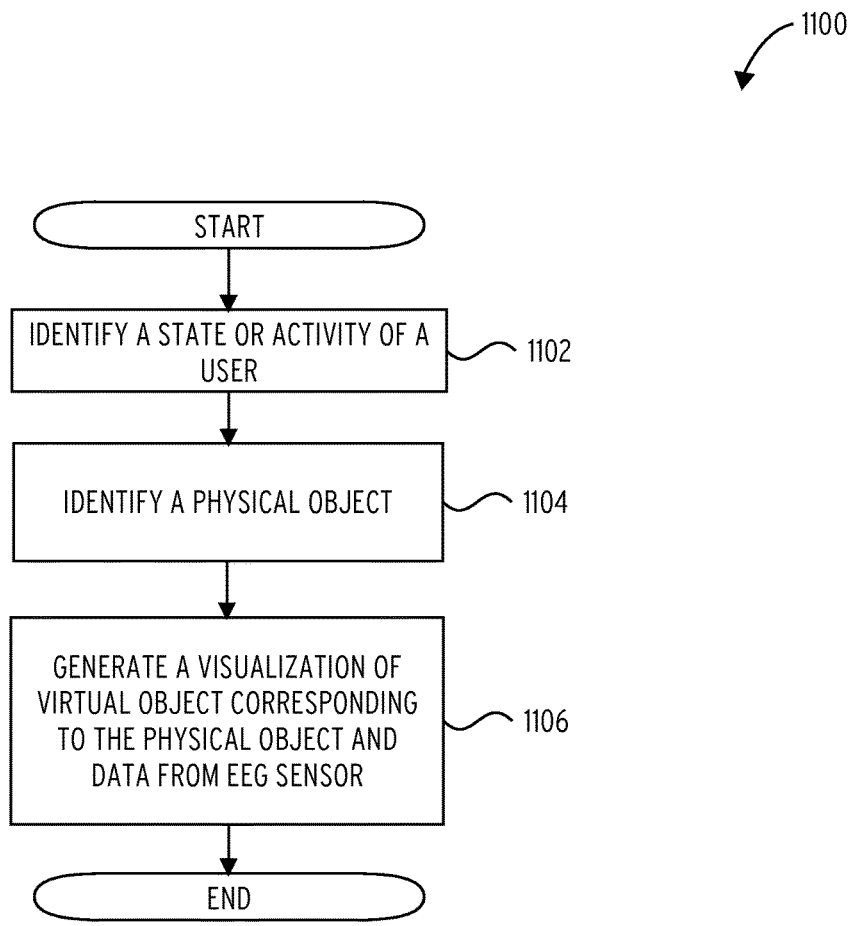
FIG. 11 is a flow diagram of a method for generating augmented reality content based on a real-time analysis of biometric data at a display device, according to some example embodiments.

FIG. 11 is a flow diagram of a method for generating augmented reality content based on a real-time analysis of biometric data at a display device, according to some example embodiments.

In block 1102, the display device 102 identifies a state (or a change of state) or activity (e.g., mental state or mental activity) of the user based on the intensity of outputs of biometric sensor 114 connected to the forehead of the user 110. The output may include, for example, electric brain waves. In one example embodiment, block 1102 may be performed using the real-time cascaded buffer application 210 of the display device 102 of FIG. 1.

In block 1104, the display device 102 identifies the physical object 112 based on an image of the physical object 112 captured with the sensors 202 of the display device 102. In one example embodiment, block 1104 may be performed by the reference identifier module 704 that identifies a visual reference on the physical object 112.

In block 1106, the augmented reality application 212 generates and displays a virtual object engaged (e.g., overlaid on top of) with an image of the physical object 112. The virtual object corresponds to the visual reference and the state or activity of the user as determined in block 1102. In one example embodiment, the virtual object generation module 706 renders the virtual object based a position of the display device 102 relative to the physical object 112.

Figure 12:
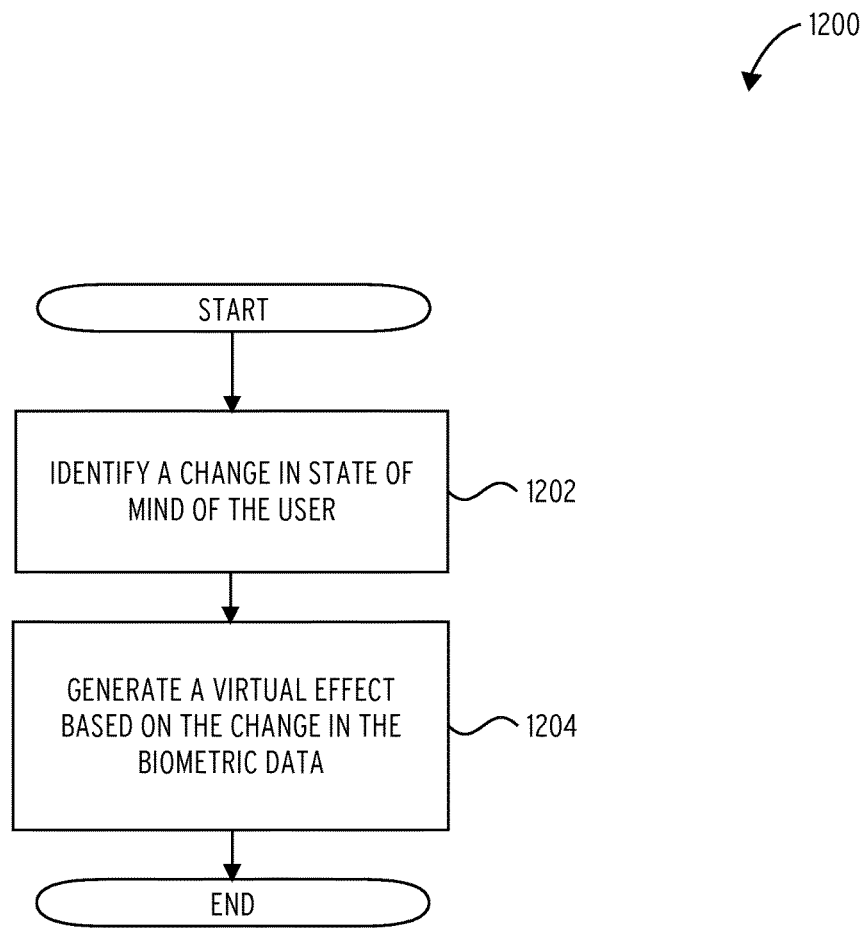
FIG. 12 is a flow diagram of a method for generating augmented reality content based real-time changes of biometric data at a display device, according to some example embodiments.

FIG. 12 is a flow diagram of a method for generating augmented reality content based real-time changes of biometric data at a display device, according to some example embodiments.

At block 1202, the display device 102 identifies a change in the level of state of mind of the user 110 based on a change in the intensity of outputs of sensors 202 coupled to the user 110. In one example embodiment, block 1202 may be performed using the real-time cascaded buffer application 210 of the display device 102 of FIG. 1.

At block 1204, the display device 102 displays a different virtual object or a virtual effect in the display based on the change in the state or activity of the user 110 (e.g., change in intensity of the output of the sensors). In other words, an action may be performed on the virtual object in the display based on the change in the state or activity of the user 110. The virtual object may be manipulated based on the change in outputs of the biometric sensor 114. For example, the color of the virtual object may change from red to blue as the user becomes more relaxed. The virtual object may spin faster as the user becomes more stressed. The door of a virtual car may open as the user becomes more visually focused on the location of the door on the display. In one example embodiment, block 1204 may be implemented with the virtual object generation module 706.

Figure 13:
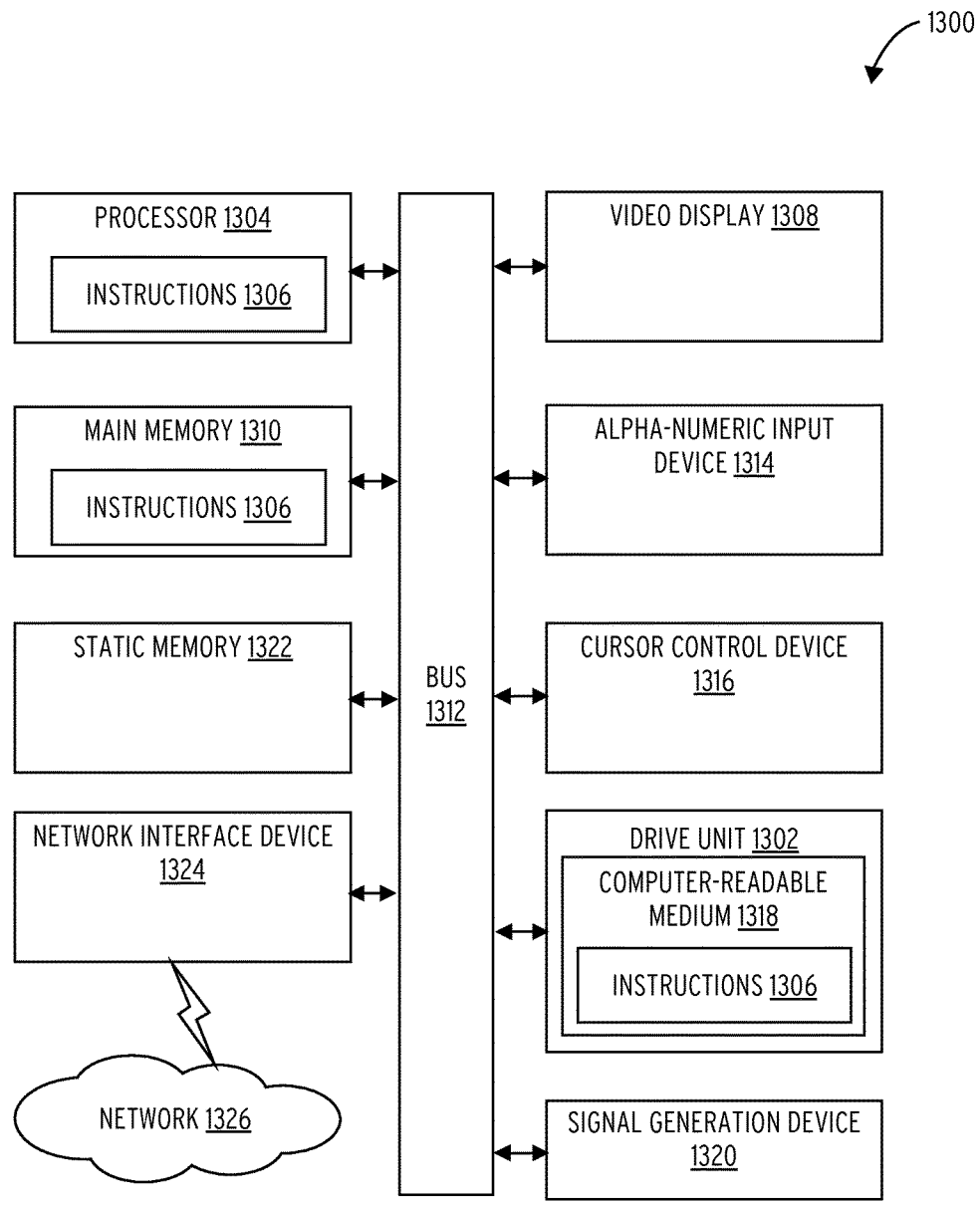
FIG. 13 a block diagram illustrating components of a machine, according to some example embodiments, able to read instructions from a machine-readable medium and perform any one or more of the methodologies discussed herein.

FIG. 13 is a block diagram illustrating components of a machine 1300, according to some example embodiments, able to read instructions 1306 from a computer-readable medium 1318 (e.g., a non-transitory machine-readable medium, a machine-readable storage medium, a computer-readable storage medium, or any suitable combination thereof) and perform any one or more of the methodologies discussed herein, in whole or in part. Specifically, the machine 1300 in the example form of a computer system (e.g., a computer) within which the instructions 1306 (e.g., software, a program, an application, an applet, an app, or other executable code) for causing the machine 1300 to perform any one or more of the methodologies discussed herein may be executed, in whole or in part.

In alternative embodiments, the machine 1300 operates as a standalone device or may be communicatively coupled (e.g., networked) to other machines. In a networked deployment, the machine 1300 may operate in the capacity of a server machine or a client machine in a server-client network environment, or as a peer machine in a distributed (e.g., peer-to-peer) network environment. The machine 1300 may be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any machine capable of executing the instructions 1306, sequentially or otherwise, that specify actions to be taken by that machine. Further, while only a single machine is illustrated, the term "machine" shall also be taken to include any collection of machines that individually or jointly execute the instructions 1306 to perform all or part of any one or more of the methodologies discussed herein.

The machine 1300 includes a processor 1304 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 1310, and a static memory 1322, which are configured to communicate with each other via a bus 1312. The processor 1304 contains solid-state digital microcircuits (e.g., electronic, optical, or both) that are configurable, temporarily or permanently, by some or all of the instructions 1306 such that the processor 1304 is configurable to perform any one or more of the methodologies described herein, in whole or in part. For example, a set of one or more microcircuits of the processor 1304 may be configurable to execute one or more modules (e.g., software modules) described herein. In some example embodiments, the processor 1304 is a multicore CPU (e.g., a dual-core CPU, a quad-core CPU, or a 128-core CPU) within which each of multiple cores behaves as a separate processor that is able to perform any one or more of the methodologies discussed herein, in whole or in part. Although the beneficial effects described herein may be provided by the machine 1300 with at least the processor 1304, these same beneficial effects may be provided by a different kind of machine that contains no processors (e.g., a purely mechanical system, a purely hydraulic system, or a hybrid mechanical-hydraulic system), if such a processor-less machine is configured to perform one or more of the methodologies described herein.

The machine 1300 may further include a video display 1308 (e.g., a plasma display panel (PDP), a light emitting diode (LED) display, a liquid crystal display (LCD), a projector, a cathode ray tube (CRT), or any other display capable of displaying graphics or video). The machine 1300 may also include an alpha-numeric input device 1314 (e.g., a keyboard or keypad), a cursor control device 1316 (e.g., a mouse, a touchpad, a trackball, a joystick, a motion sensor, an eye tracking device, or other pointing instrument), a drive unit 1302, a signal generation device 1320 (e.g., a sound card, an amplifier, a speaker, a headphone jack, or any suitable combination thereof), and a network interface device 1324.

The drive unit 1302 (e.g., a data storage device) includes the computer-readable medium 1318 (e.g., a tangible and non-transitory machine-readable storage medium) on which are stored the instructions 1306 embodying any one or more of the methodologies or functions described herein. The instructions 1306 may also reside, completely or at least partially, within the main memory 1310, within the processor 1304 (e.g., within the processor's cache memory), or both, before or during execution thereof by the machine 1300. Accordingly, the main memory 1310 and the processor 1304 may be considered machine-readable media (e.g., tangible and non-transitory machine-readable media). The instructions 1306 may be transmitted or received over a network 1326 via the network interface device 1324. For example, the network interface device 1324 may communicate the instructions 1306 using any one or more transfer protocols (e.g., hypertext transfer protocol (HTTP)).

In some example embodiments, the machine 1300 may be a portable computing device (e.g., a smart phone, tablet computer, or a wearable device), and have one or more additional input components (e.g., sensors or gauges). Examples of such input components include an image input component (e.g., one or more cameras), an audio input component (e.g., one or more microphones), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), a biometric input component (e.g., a heartrate detector or a blood pressure detector), and a gas detection component (e.g., a gas sensor). Input data gathered by any one or more of these input components may be accessible and available for use by any of the modules described herein.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the computer-readable medium 1318 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing the instructions 1306 for execution by the machine 1300, such that the instructions 1306, when executed by one or more processors of the machine 1300 (e.g., processor 1304), cause the machine 1300 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible and non-transitory data repositories (e.g., data volumes) in the example form of a solid-state memory chip, an optical disc, a magnetic disc, or any suitable combination thereof. A "non-transitory" machine-readable medium, as used herein, specifically does not include propagating signals per se. In some example embodiments, the instructions 1306 for execution by the machine 1300 may be communicated by a carrier medium. Examples of such a carrier medium include a storage medium (e.g., a non-transitory machine-readable storage medium, such as a solid-state memory, being physically moved from one place to another place) and a transient medium (e.g., a propagating signal that communicates the instructions 1306).

The following enumerated embodiments describe various example embodiments of methods, machine-readable media, and systems (e.g., machines, devices, or other apparatus) discussed herein.

A first embodiment provides a server comprising:
a processor; and
a memory storing instructions that, when executed by the processor, configure the server to:
detect biometric data having different types of waves using at least two electrodes configured to be connected to a user; and
compute, using a hardware processor, features of the biometric data over a plurality of sampling periods;
form a cascading buffer based on the plurality of sampling periods from the computed features of the biometric data;
dynamically monitor shifting baselines of the computed features over the plurality of sampling periods in the cascading buffer; and
identify a change in the state of the user based on shifting baselines in the cascading buffer.

A second embodiment provides a server configured to:
determine a plurality of trends of the computed features in the cascading buffer over the plurality of sampling periods;
compare the trends based on a same or other type of waves at a same or other sampling period in the cascading buffer;
compute a plurality of ratios based on the comparison of the trends;
normalize the computed plurality of ratios based on the plurality of trends over the plurality of sampling periods;
scale the normalized computed plurality of ratios; and
identify the change in the state of the user based on the scaled normalized computed plurality of ratios.

A third embodiment provides a server, wherein the biometric data include oscillatory brain wave data, the different types of waves including an alpha type of wave, a beta type of wave, a delta type of wave, a theta type of wave, a slow-wave type of wave, a gamma type of wave, and a high-gamma type of wave, the slow-wave type of wave having less than 1 Hz.

A third embodiment provides a server, wherein the sampling periods include vary sampling periods.

A fourth embodiment provides a server configured to:
identify a change in an activity of the user based on the scaled normalized computed features; and
identify an event in the activity of the user based on the scaled normalized computed features A fifth embodiment provides a server configured to:
identify the change in the state of the user over successively longer sampling periods.

A sixth embodiment provides a server configured to:
filter the biometric data to attenuate electrical interference;
apply a Fourier transform operation on the filtered biometric data over a sliding window of the sampling period; and
compute a variability metric over the sampling period based on an output of the Fourier transform operation.

A seventh embodiment provides a server configured to:
identify the change in the state of the user based on a trend of the scaled waves over the multiple sampling periods.

An eighth embodiment provides a server configured to:
capture a reference identifier from a physical object with a camera in a head mounted device;
identify a virtual object associated with the reference identifier;
display the virtual object in a display of the head mounted device; and
in response to a relative movement between the head mounted device and the physical object caused by a user, modify the virtual object based on the change in the state of the user of the head mounted device.

What is claimed is:

1. A method comprising:
    detecting biometric data representing different types of waves using at least two electrodes configured to be connected to a user;
    computing, using a hardware processor, features of the biometric data over a plurality of sampling periods;
    forming a cascading buffer based on the plurality of sampling periods from the computed features of the biometric data;
    dynamically monitoring shifting baselines of the computed features over the plurality of sampling periods in the cascading buffer; and
    identifying a change in the state of the user based on shifting baselines in the cascading buffer.

2. The method of claim 1, wherein the biometric data include oscillatory brain wave data, the different types of waves including an alpha type of wave, a beta type of wave, a delta type of wave, a theta type of wave, a slow-wave type of wave, a gamma type of wave, and a high-gamma type of wave, the slow-type of wave having a frequency less than 1 Hz.

3. The method of claim 1, wherein the sampling periods include varying sampling periods.

4. The method of claim 1, further comprising:
    identifying the change in the state of the user over successively longer sampling periods.

5. The method of claim 1, further comprising:
    filtering the biometric data to attenuate electrical interference;
    applying a Fourier transform operation on the filtered biometric data over a sliding window of the plurality of sampling periods; and
    computing a variability metric over the plurality of sampling periods based on an output of the Fourier transform operation.

6. The method of claim 1, further comprising:
    disposing the at least two electrodes in a head mounted device.

7. The method of claim 6, further comprising:
    capturing a reference identifier from a physical object with a camera in the head mounted device;
    identifying a virtual object associated with the reference identifier;
    displaying the virtual object in a display of the head mounted device; and in response to a relative movement between the head mounted device and the physical object caused by a user, modifying the virtual object based on the change in the state of the user of the head mounted device.

8. A server comprising:
a processor; and
a memory storing instructions that, when executed by the processor, configure the server to:
  detect biometric data representing different types of waves using at least two electrodes configured to be connected to a user;
  compute, using a hardware processor, features of the biometric data over a plurality of sampling periods;
  form a cascading buffer based on the plurality of sampling periods from the computed features of the biometric data;
  dynamically monitor shifting baselines of the computed features over the plurality of sampling periods in the cascading buffer; and
  identify a change in the state of the user based on shifting baselines in the cascading buffer.

9. The server of claim 8, wherein the biometric data include oscillatory brain wave data, the different types of waves including an alpha type of wave, a beta type of wave, a delta type of wave, a theta type of wave, a slow-wave type of wave, a gamma type of wave, and a high-gamma type of wave, the slow-wave type of wave having a frequency less than 1 Hz.

10. The server of claim 8, wherein the sampling periods include vary varying sampling periods.

11. The server of claim 8, wherein the instructions further configure the server to:
  identify the change in the state of the user over successively longer sampling periods.

12. The server of claim 8, wherein the instructions further configure the server to:
  filter the biometric data to attenuate electrical interference;
  apply a Fourier transform operation on the filtered biometric data over a sliding window of the plurality of sampling periods; and
  compute a variability metric over the plurality of sampling periods based on an output of the Fourier transform operation.

13. The server of claim 8, wherein the instructions further configure the server to:
  capture a reference identifier from a physical object with a camera in a head mounted device;
  identify a virtual object associated with the reference identifier;
  display the virtual object in a display of the head mounted device; and
  in response to a relative movement between the head mounted device and the physical object caused by a user, modify the virtual object based on the change in the state of the user of the head mounted device.

14. A non-transitory computer-readable storage medium, the computer-readable storage medium including instructions that when executed by a computer, cause the computer to:
  detect biometric data representing different types of waves using at least two electrodes configured to be connected to a user;
  compute, using a hardware processor, features of the biometric data over a plurality of sampling periods;
  form a cascading buffer based on the plurality of sampling periods from the computed features of the biometric data;
  dynamically monitor shifting baselines of the computed features over the plurality of sampling periods in the cascading buffer; and
  identify a change in the state of the user based on shifting baselines in the cascading buffer.

* * * * *

UNITED STATES PATENT AND TRADEMARK OFFICE
CERTIFICATE OF CORRECTION

PATENT NO. : 9,585,581 B1
APPLICATION NO. : 14/870900
DATED : March 7, 2017
INVENTOR(S) : Mullins et al.

Page 1 of 1

It is certified that error appears in the above-identified patent and that said Letters Patent is hereby corrected as shown below:

On the Title Page

In item (22), in "Filed", in Column 1, Line 1, after "2015", insert --¶(65) Prior Publication Data US 2017/0086695 A1 Mar. 30, 2017--

In the Claims

In Column 23, Line 30, in Claim 10, after "include", delete "vary"

Signed and Sealed this
Fifth Day of May, 2020

Andrei Iancu
*Director of the United States Patent and Trademark Office*